United States Patent
Makinson et al.

(10) Patent No.: US 7,086,399 B2
(45) Date of Patent: Aug. 8, 2006

(54) APPARATUS FOR DELIVERY OF HUMIDIFIED GASES THERAPY, ASSOCIATED METHODS AND ANALYSIS TOOLS

(75) Inventors: Ian Douglas Makinson, Auckland (NZ); Alex Young, Auckland (NZ); David Alan Bond, Pukekohe (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 47 days.

(21) Appl. No.: 10/446,594

(22) Filed: May 28, 2003

(65) Prior Publication Data

US 2004/0016430 A1    Jan. 29, 2004

(30) Foreign Application Priority Data

May 29, 2002    (NZ) ...................................... 519244

(51) Int. Cl.
*A61M 16/00*    (2006.01)
(52) U.S. Cl. ........................... 128/204.21; 128/204.18; 128/204.23
(58) Field of Classification Search ........... 128/201.13, 128/203.12, 203.16, 203.17, 203.26, 203.27, 128/203.29, 204.14, 204.17, 204.18, 206.21, 128/206.28, 207.11, 920, 923, 204.22, 204.23, 128/200.11, 200.14, 204.21; 239/338; 261/DIG. 65, 261/129, 154; 122/4 A, 4 R, 5.5 A, 7 B, 122/13.01, 13.3–19.2, 33, 487, DIG. 7; 422/123–124
See application file for complete search history.

(56) References Cited

U.S. PATENT DOCUMENTS

| | | | | |
|---|---|---|---|---|
| 5,163,423 A | * | 11/1992 | Suzuki .................. | 128/203.26 |
| 5,537,997 A | | 7/1996 | Mechlenburg et al. | |
| 5,890,490 A | * | 4/1999 | Aylsworth et al. ..... | 128/203.12 |
| 5,947,115 A | * | 9/1999 | Lordo et al. ........... | 128/200.24 |
| 5,954,050 A | * | 9/1999 | Christopher ........... | 128/204.23 |
| 6,050,260 A | * | 4/2000 | Daniell et al. ......... | 128/204.22 |
| 6,279,574 B1 | * | 8/2001 | Richardson et al. ... | 128/204.18 |

FOREIGN PATENT DOCUMENTS

GB    2338420    12/1999

* cited by examiner

*Primary Examiner*—Henry Bennett
*Assistant Examiner*—Amadeus Lopez
(74) *Attorney, Agent, or Firm*—Trexler, Bushnell, Giangiorgi, Blackstone & Marr, Ltd.

(57) ABSTRACT

Apparatus for delivery of humidified gases therapy includes a humidifier. A recorder records. An output interface allows for outputting of the recorded data. The recorder may also record data indicative of patient compliance with the humidified gases therapy. The apparatus may determine patient compliance from sensed delivered flow.

Recorded humidity and compliance data retrieved from the apparatus are useful in methods for improving the efficacy of humidified gases therapy or diagnosing problems with the efficacy of humidified gases therapy.

12 Claims, 9 Drawing Sheets

| HC221 Compliance Report (LCD) |
|---|

Patient  ID: 1212

Name: TOM SMITH  
Address: 23 South St  
Pacific Point  
Auckland  
New Zealand

Age: 45  
Sex: male  
Height: 1.8M  
Weight: 100kg  
BMI: 35

Phone: 233-4567  
Fax 233-456  
EMail: john.atkins@fphcare.co.nz .

Insurance Carrier: Kaiser  
Phone: 445-4567  
Fax: 445-4568  
Policy Number: OSA3456  
Sleep Lab: F&PHC

| HomeCare Provider | Physician |
|---|---|
| Checked By:<br>Address: | Name: DR JOHN<br>Address: 4545 Insurance Blvd<br>Center City<br>Auckland<br>New Zealand |
| Phone:<br>Fax:<br>EMail: | Contact: Nurse Johnson<br>EMail: doug.makinson@fphcare.co.nz |

HC 221

Serial Number: SAMPLE FILE  
Prescribed Pressure Setting: 10.0

Initial Setup Date: Oct-24-2001  
Mask Type on HC221: Aclaim

Current Humidity Setting

0

Average Hours Compliant Per Day 5.4

Total Hours with HC221 switched on

| HC221 Compliance Report (Download) |
|---|

Patient                                   ID: 1212

Name: TOM SMITH                    Age: 45
   Address: 23 South St                    Sex: male
            Pacific Point             Height: 1.8M
            Auckland                 Weight: 100kg
            New Zealand                  BMI: 35

Phone: 233-4567
        Fax: 233-456
     EMail: john.atkins@fphcare.co.nz Insurance Carrier: Kaiser
      Phone: 445-4567
        Fax: 445-4568
Policy Number: OSA3456
   Sleep Lab: F&PHC

HomeCare Provider                         Physician
Name:                                         Name: DR JOHN
Address:                                      Address: 4545 Insurance Blvd
                                                                              Center City
                                                                              Auckland
                                                                              New Zealand Phone:                                        Contact: Nurse Johnson
Fax:                                          EMail: doug.makinson@fphcare.co.nz
EMail:

HC 221        Checked By:

Serial Number: SAMPLE FILE
       Prescribed Pressure Setting: 10.0

Initial Setup Date: Oct-24-2001
                  Mask Type: Aclaim 30, 60, 90 day History from Jan-30-2003 Thu

|  | 1 - 30 Days | 30 - 60 Days | 60 - 90 Days |
|---|---|---|---|
| Average Hours Compliant Per Day Used | 6.0 | 6.0 | 6.0 |
| Days with more than 4hr Compliance | 30 | 60 | 90 |
| Average Humidity Setting | 1.5 | 1.5 | 1.5 |

Total Hours with HC221 switched on for selected period
  84
Average hours compliant per day used for selected period
  6.1

APPARATUS FOR DELIVERY OF HUMIDIFIED GASES THERAPY, ASSOCIATED METHODS AND ANALYSIS TOOLS

BACKGROUND TO THE INVENTION

1. Field of the Invention

This invention relates to apparatus for delivery of humidified gases therapy and in particular, though not solely to humidified Positive Airway Pressure (PAP) apparatus used in the treatment of Obstructive Sleep Apnea (OSA).

2. Summary of the Prior Art

OSA is a sleep disorder which affects an estimated 5% of the population in which muscles which normally hold the airway open, relax and ultimately collapse, sealing the airway. The sleep pattern of an OSA sufferer is characterised by repeated sequences of snoring, breathing difficulty, lack of breathing, waking with a start and then returning to sleep. Often the sufferer is unaware of this pattern occurring. Sufferers of OSA usually experience daytime drowsiness and irritability due to a lack of good continuous sleep.

In an effort to treat OSA sufferers, a technique known as Continuous Positive Airway Pressure (CPAP) was devised. A CPAP device consists of a gases supply (or blower) with a conduit connected to supply pressurised gases to a patient, usually through a nasal mask. The pressurised air supplied to the patient effectively assists the muscles to keep the patient's airway open, eliminating the typical OSA sleep pattern.

The use of a CPAP system is known to have side effects such as dehydration of the airways and nasal passages which may lead to Rhinitis (inflammation of the nasal passages). The side effects mean that the patient is less likely to comply with his or her CPAP therapy and the therapy itself may cause an increase in nasal resistance as a response to the high air flow, degrading the pressure level applied to the airway and thereby reducing the effectiveness of the therapy. Accordingly, humidified CPAP systems have been developed. One example is described in U.S. Pat. No. 5,537,997 assigned to Respironics Inc. in which a humidifier is incorporated with the CPAP system so that the patient receives humidified gases. Another example is shown in GB 2338420.

While these humidified systems improve patient comfort when properly used, inappropriate setting or lack of activation of the humidifier component of the CPAP system reduces the comfort benefits. It is known that patients or users are prone to failing to use the system where comfort levels are poor, with users frequently failing to comply within a structured regime of treatment.

In a first aspect the invention may broadly be said to consist in an apparatus for delivery of humidified gases therapy, said apparatus including:

a humidifier, said humidifier having a humidity setting selector, operable by said patient to set and adjust a desired humidity level, a blower, said blower having a range of operating speeds, and delivering a substantially constant pressure across a wide flow range, for an unvaried operating speed, a flow sensor providing an output indicative of flow delivered by said apparatus, means for producing user compliance data, calculated from said output of said flow sensor and said operating speed of said blower, data recording means, said data recording means recording humidity data and said user compliance data, said humidity data indicative of the humidity of gases delivered by the apparatus, an output interface means for outputting said recorded user compliance data and humidity data.

In a second aspect the invention may broadly be said to consist In a method of diagnosing causes of ineffective humidified gases therapy comprising the steps of:

retrieving logged humidity data and logged patient compliance data from an apparatus, comparing said patient compliance data with said humidity data, and determining inadequate or excessive humidity as a potential cause of said inadequat; treatment based on said comparisons.

In a third aspect the invention may broadly be said to consist in a method of improving efficacy of humidified gases therapy comprising the steps of:

retrieving logged humidity data and logged patient compliance data from an apparatus, comparing said patient compliance data with said humidity data, and recommending alterations to said therapy based on said comparisons.

SUMMARY OF THE INVENTION

It is therefore an object of the present invention to provide apparatus for delivery of humidified gases therapy and/or methods and/or analysis tools which will at least go some way towards providing users and/or healthcare providers with a means of assessing and monitoring one of the causes of non compliance.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

One preferred form of the invention will now be described with reference to the accompanying drawings.

DETAILED DESCRIPTION

Figure 1:
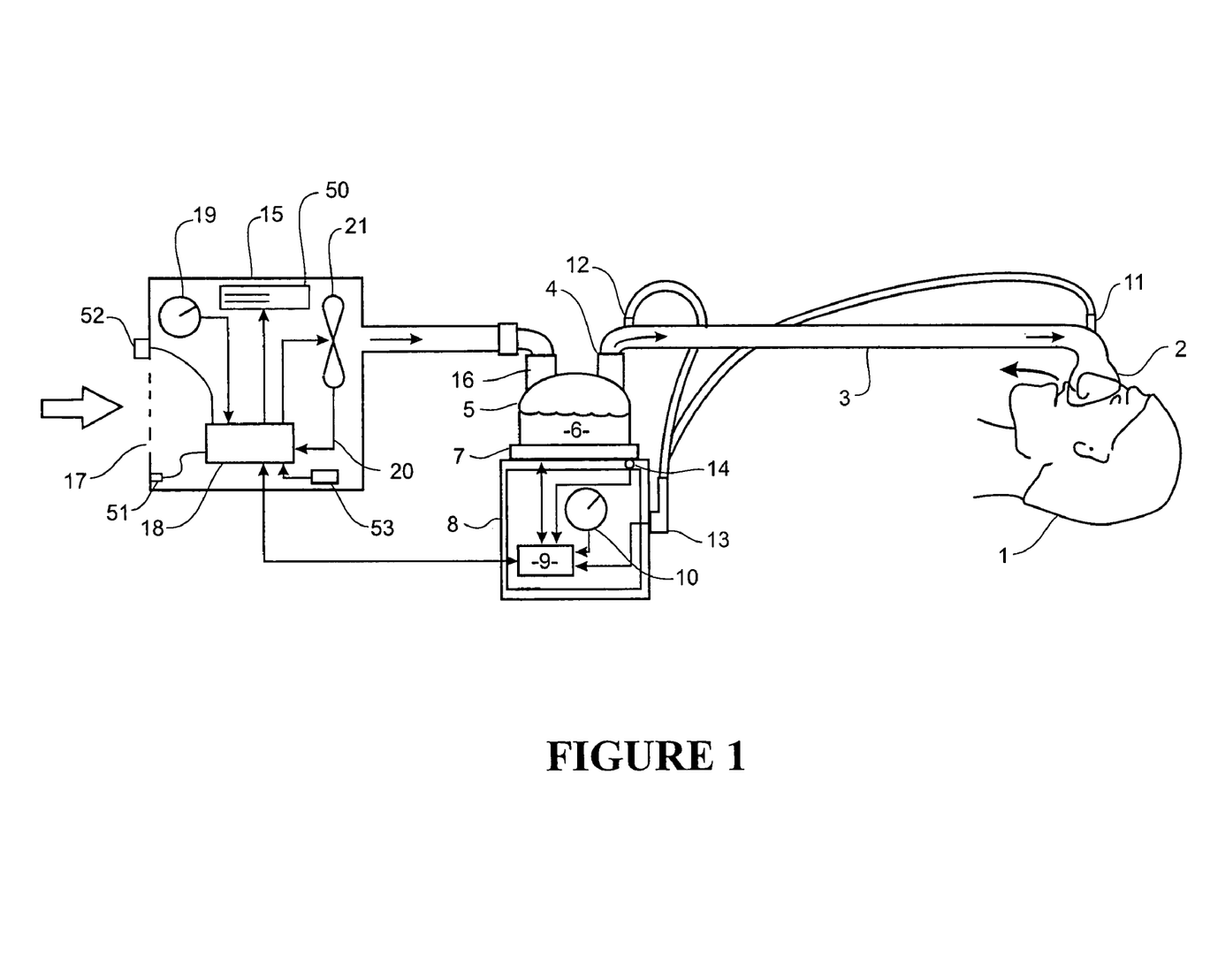
FIG. 1 is a block diagram of a humidified Continuous Positive Airway Pressure (CPAP) system in accordance with a preferred embodiment of the present invention.

With reference to FIG. 1 an exemplary humidified Continuous Positive Airway Pressure (CPAP) system is shown in which a patient 1 is receiving humidified and pressurised gases through a nasal mask 2 connected to a humidified gases transportation pathway or inspiratory conduit 3. It should be understood that the present invention, however, is not limited to the delivery of CPAP gases but is also applicable to other types of gases delivery systems such as variable positive airway pressure) and bi-level positive airway pressure systems, or humidified oxygen therapy.

Inspiratory conduit 3 is connected to the outlet 4 of a humidification chamber 5 which contains a volume of water 6. Inspiratory conduit 3 may contain heating means or heater wires (not shown) which heat the walls of the conduit to ensure a constant humidity profile along the conduit and therefore reduce condensation of humidified gases within the conduit. Humidification chamber 5 is formed from a plastic material and has a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature, humidity and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. It should be noted that there is a relationship between the humidity of the gases in humidification chamber 5 and the temperature of the heater plate 7.

Exhaled gases from the patient's mouth are passed directly to ambient surroundings in FIG. 1.

Blower 15 is provided with a variable speed fan 21 which draws air or other gases through blower inlet 17 producing a resultant gases flow rate. The speed of variable speed fan 21 is controlled by a further control means or electronic controller 18 (or alternatively the function of controller 18 could be carried out by controller 9) in response to inputs from controller 9 and a user set predetermined required level (preset value) of pressure via dial 19.

Figure 2:
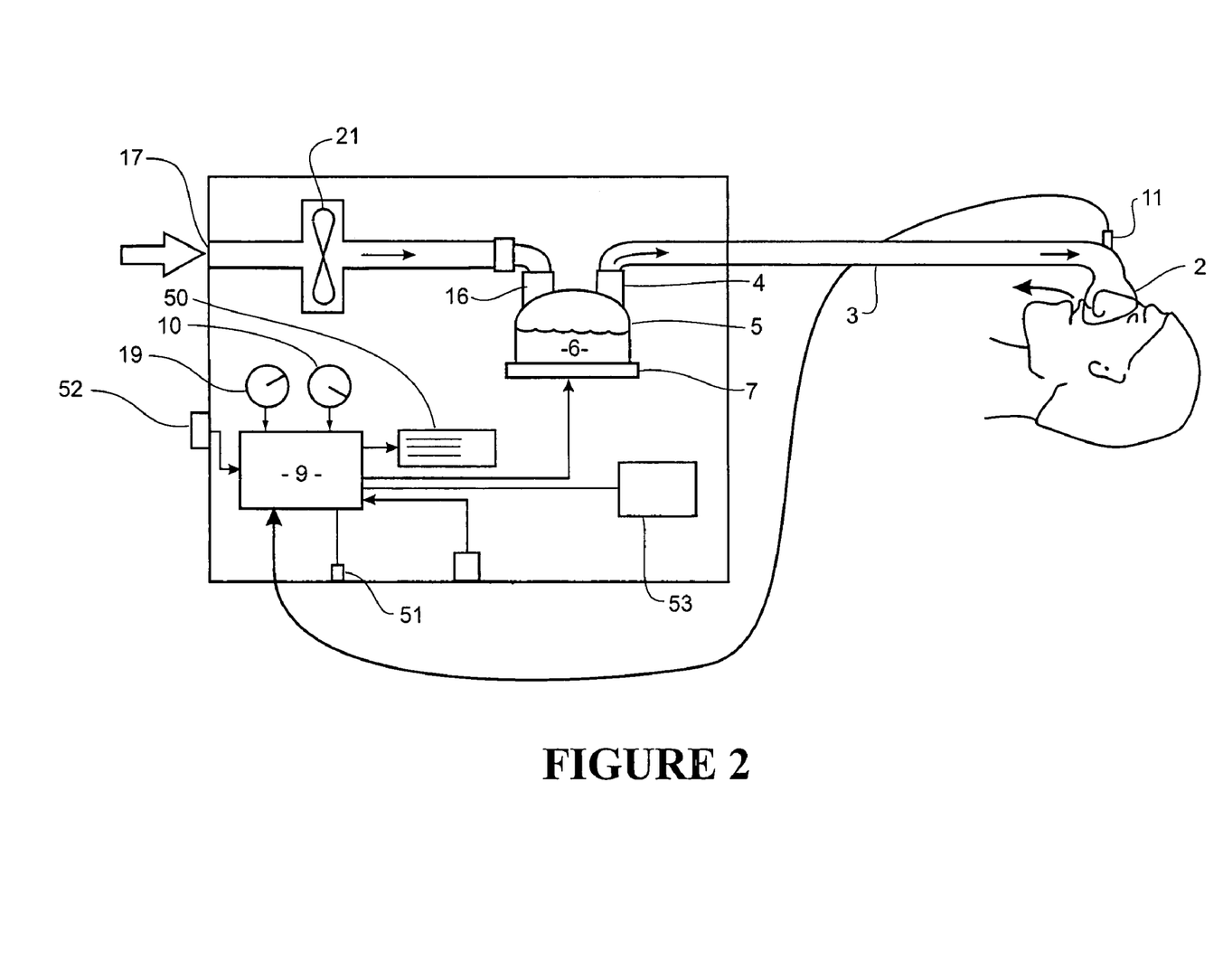
FIG. 2 is a block diagram of a humidified CPAP system in accordance with a further preferred embodiment of the present invention.

Another exemplary humidified CPAP system is shown in FIG. 2 where the humidifier has been incorporated within blower 15 so that the system comprises only one main component connected to the patient via the same conduit 3 and nose mask 2. Only one controller 9 is required in this embodiment. All reference numerals common to FIG. 1 represent the same features in FIG. 2.

According to the preferred embodiment of the present invention the controller 9 (or 18) in the embodiment of FIG. 1 is preferably programmed to perform a recording function for compliance and humidity data. In particular the controller 9 includes data storage for storing the compliance and humidity data, and at least one output interface for allowing retrieval of some or all of the stored data. The preferred output interfaces include display on a local LCD display 50 and download via optical, electrical or wireless pickup (e.g. serial port 51) to a receiving device for direct upload to an analysis and reporting software package.

In the preferred form of the present invention, user set humidity input via dial 10 is utilised to represent humidity, however, any suitable humidity sensor could alternatively be used.

Figure 4:
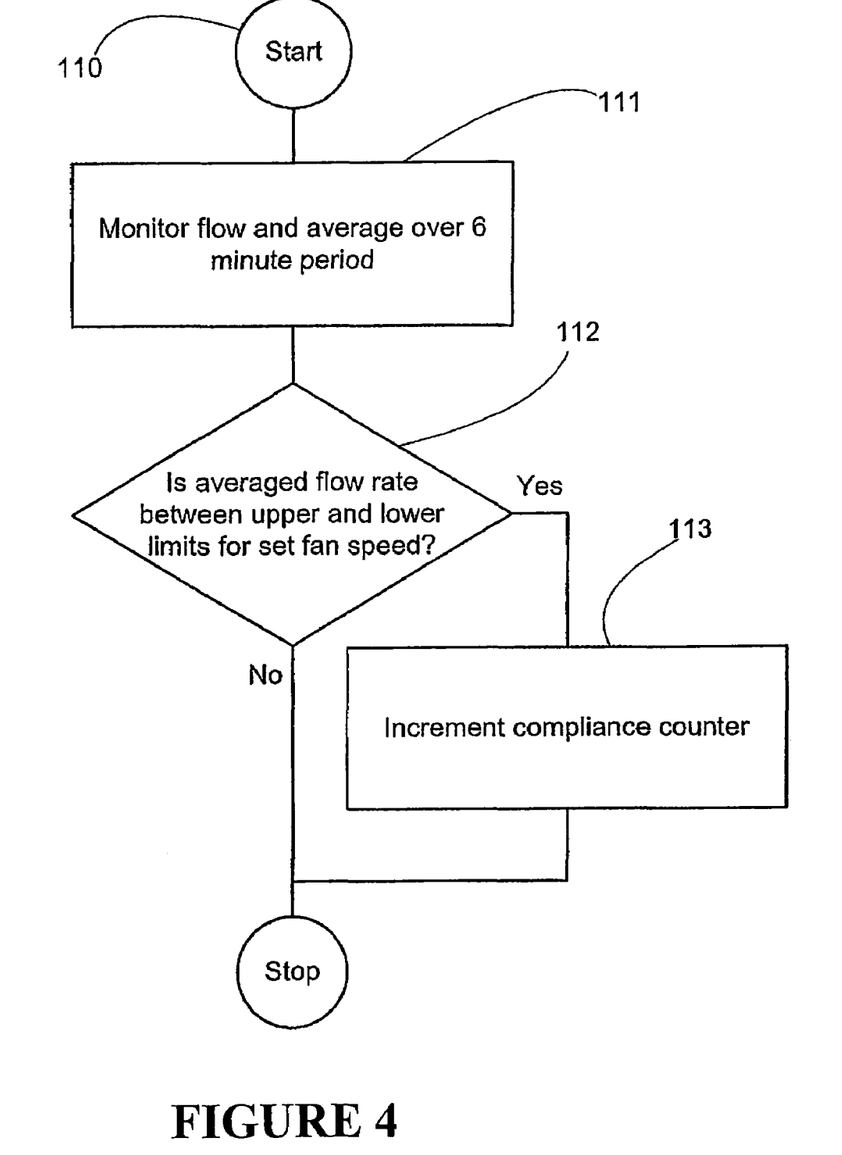
FIG. 4 is a flow diagram depicting a compliance monitoring process performed by the controller of the apparatus according to a preferred embodiment of the present invention.
Figure 5:
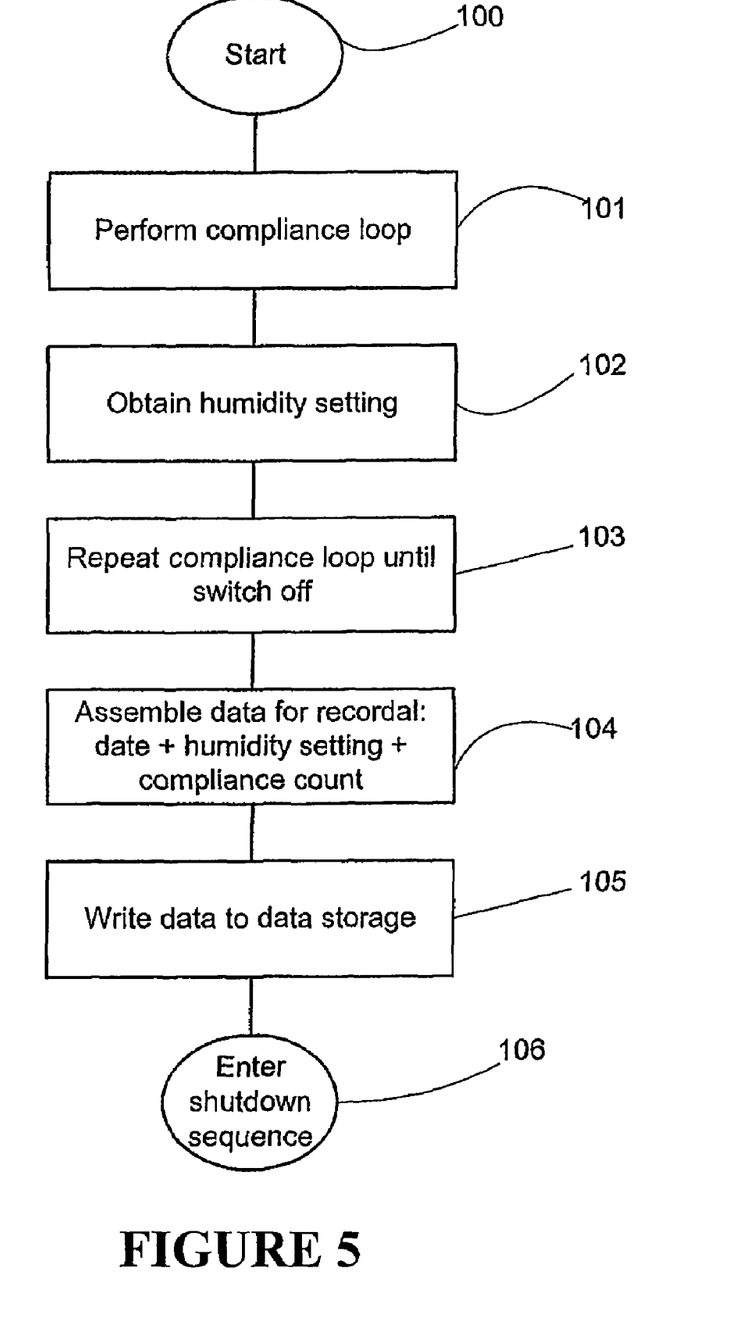
FIG. 5 is a flow diagram depicting a data gathering and storing process performed by the controller.

The controller 9 is programmed to perform a data gathering and recording process illustrated in FIG. 5. The data gathering and recording process begins at step 100 as soon as the apparatus is activated, and commences a compliance monitoring loop at step 101. The compliance monitoring loop is depicted in FIG. 4 and is performed over a six minute period. At the end of this first six minute period the controller obtains an indication of the humidity or intended humidity at step 102. Preferably step 102 includes obtaining a value corresponding to the present humidity setting as set on dial 10.

The controller then proceeds at step 103 to repeat the compliance monitoring loop of FIG. 4 until the user deactivates the apparatus. Upon receiving a deactivation signal from on off button 52 the controller proceeds into a shutdown sequence. The shutdown sequence includes assembling a data string for recordal in a non volatile data store at step 103. The data string includes a date read from system clock 53, the humidity setting obtained at step 102 and the present compliance count as incremented in successive iterations of the compliance monitoring loop. At step 105 the controller 9 writes the data string to the non volatile data storage before entering shutdown mode at step 106.

The compliance monitoring loop as performed at step 101 and repeatedly performed at step 103 is illustrated in more detail in FIG. 4. The compliance monitoring loop starts at step 110 by commencing to monitor the flow indicated by sensor 12 over a six minute period. At step 111 the controller determines an average flow over the six minute period. At step 112 the controller compares the flow average from step 111 to an upper and lower flow limit applicable to the presently set fan speed. If the controller determines at step 112 that the average six minute flow is between the upper and lower limits the controller increments a compliance counter at step 113 before finishing the compliance monitoring loop. Otherwise the controller finishes the compliance monitoring loop without incrementing the compliance counter.

Figure 3:
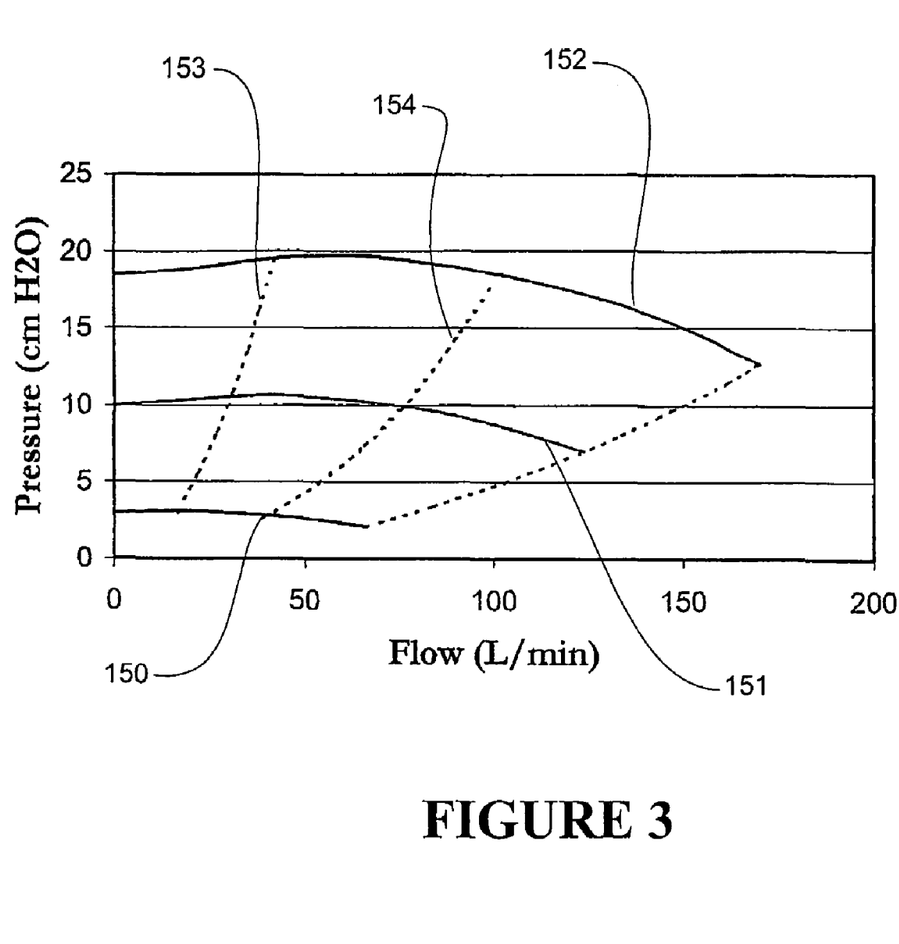
FIG. 3 is an example graph of Pressure v Flow curves demonstrating a preferred method for determining patient compliance.

Referring to FIG. 3 a chart of Pressure v Flow shows a set of pressure flow curves for a typical apparatus according to the preferred embodiment of the present invention. According to the preferred embodiment of the present invention the blower 15 is operated with a constant fan speed at any one time. The fan is such that the blower output pressure is reasonably constant across a generally effective flow range. Typical pressure flow curves 150, 151 and 152 are shown for fan speeds which correspond to pressures of 3 cm H2O, 10 cm H2O and 18 cm H2O respectively, with blocked flow (0 L/min). These curves encompass the typical widest operating range required for a humidified gases delivery apparatus according to the present invention.

For determining compliance it is considered that a normal range of flow is made up of a mask bias flow and any mouth or mask leak that may be present. The mask bias flow is determined by the mask that is used by the user or patient but is typically equivalent to the flow through a 4 millimetre diameter hole in an otherwise blocked conduit. Curve 153 is a pressure flow curve representing the approximate flow that would flow through the 4 millimetre diameter hole for the given internal pressure. By experimentation the applicant has selected that a patient can be considered compliant if the mask bias flow together with any mouth or mask leak gives a total flow less than the flow through a 6.8 millimetre diameter hole. For reference this hole gives a flow of 100 L/min for the fan speed setting of curve 152. Pressure flow curve 154 represents this upper flow limit.

A flow is considered to indicate compliance if, on the pressure flow curve for its set fan speed, it is between the lower limit 153 and upper limit 154. If the flow is beyond the upper limit 154 then this indicates an excessive flow due to mask removal or excessive mouth or mask leaks, rendering the therapy ineffective. If the flow is below the lower limit this will usually indicate a hose blockage or other intentional interference, also indicating ineffective therapy.

In a preferred form of the invention the controller 9 is also programmed to record the device set pressure in addition to the humidity setting. In a preferred form the set pressure corresponds with a set fan speed, with the actual delivered pressure varying according to the flow restriction. Higher pressures indicate higher flow rates, and lower absolute humidity for a given humidity setting, when the humidity setting corresponds with heater plate temperature. Where the humidifier accounts for flow rate and controlling the heater plate temperature, or operates with absolute humidity feedback, then the directly recorded humidity setting may be more in accordance with the absolute humidity being delivered and recordal of the set pressure is less useful for assessing optimal humidity levels. However it may still be useful to record for other comfort assessment.

Where the system includes a flow rate sensor or ambient temperature sensor data from these sensors may also be used to advantage to better approximate the humidity being delivered to the patient. Data corresponding with the measured average flow or average ambient temperature for each session may be included with the humidity setting in the data string written to the non volatile data storage before entering the shutdown mode. Alternatively the humidity setting, flow and/or ambient temperature data may be utilised in a calculation within the controller 9 to provide a parameter which is a better indicator of the delivered humidity than the humidity setting alone. This parameter may be recorded as the parameter indicative of delivered humidity in the data string. Where this calculation is undertaken within the controller 9 it may be undertaken at the end of a session based on average readings or may be the average of a series of calculations made throughout the session.

According to the preferred embodiment of the present invention compliance and humidity data may be extracted from the apparatus in one of several alternative forms. In a first form the data may be extracted directly by a user from LCD screen 50. The controller 9 is programmed to display information on the LCD display when the unit is turned on. In particular the controller 9 is programmed to display the total hours that the unit has been used since the data store was last reset, the average number of complied hours per night that the unit has been used and a check sum which is an encryption of the first two numbers.

In a second form the data may be downloaded from the communications port 52 to a clinician's computer running compliance reporting software according to another aspect of the present invention. The downloaded data includes the complete data held by the data store. The controller 9 is programmed to clear the data store in response to commands from the compliance reporting software. The compliance reporting software issues such commands in response to a software user selection that the device should be reset. Preferably the controller 9 is also programmed to reset the data store in response to a preset button sequence and/or button combination on the device. In the preferred form of the invention the controller 9 is programmed to store data consecutively in the data store, returning to the beginning once the storage limit is reached and subsequently overwriting the earlier stored data. The data store size is sufficient to store data representing a considerable period of use, and the compliance reporting software compiles a permanent record of the downloaded data. Accordingly the data store of the device will generally only require resetting if the device is to be supplied to a new patient.

Data extracted from the apparatus may be analysed with the assistance of reporting software according to a further aspect of the present invention. The reporting software may preferably receive data obtained in either the above two forms.

The reporting software includes an interface for entry of data downloaded from the LCD display. The reporting software is programmed to verify that, for a set of entered data, the check sum matches the check sum expected from the other data entered. The data entry interface also includes an entry field for entering a humidity setting read directly from the humidity controller dial. The reporting software is programmed to store entered data in association with a patient record which includes patient detail and historical summary data from the LCD display and humidity control setting. The reporting software is programmed to produce a report including patient details, the summary data and whether the check sum was verified. An example compiled report complied from LCD data is presented as FIG. 6.

Figure 7A:
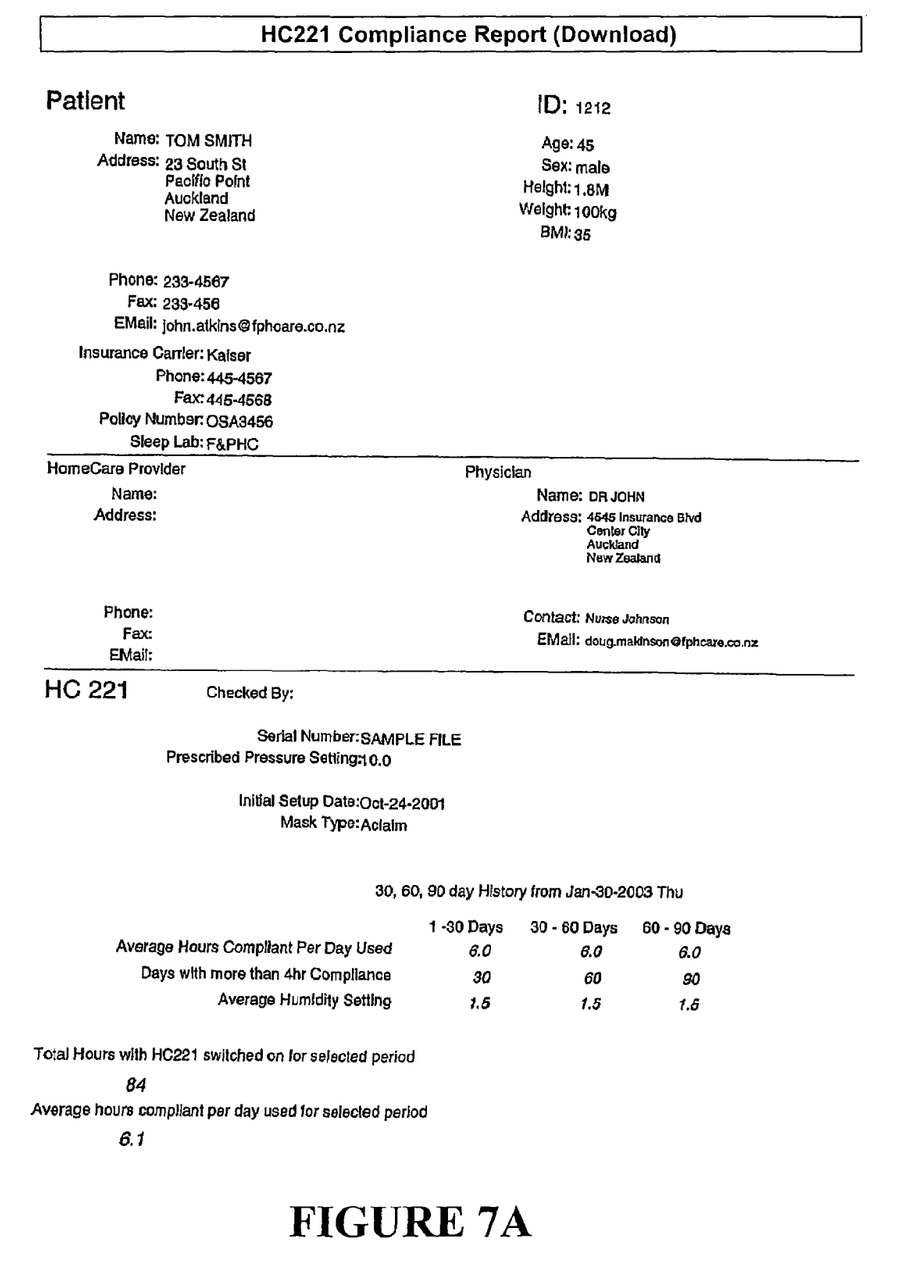
FIGS. 7A, 7B and 7C combined, show an example of a patient summary report based on compliance and humidity data downloaded from a preferred apparatus according to the present invention.
Figure 7B:
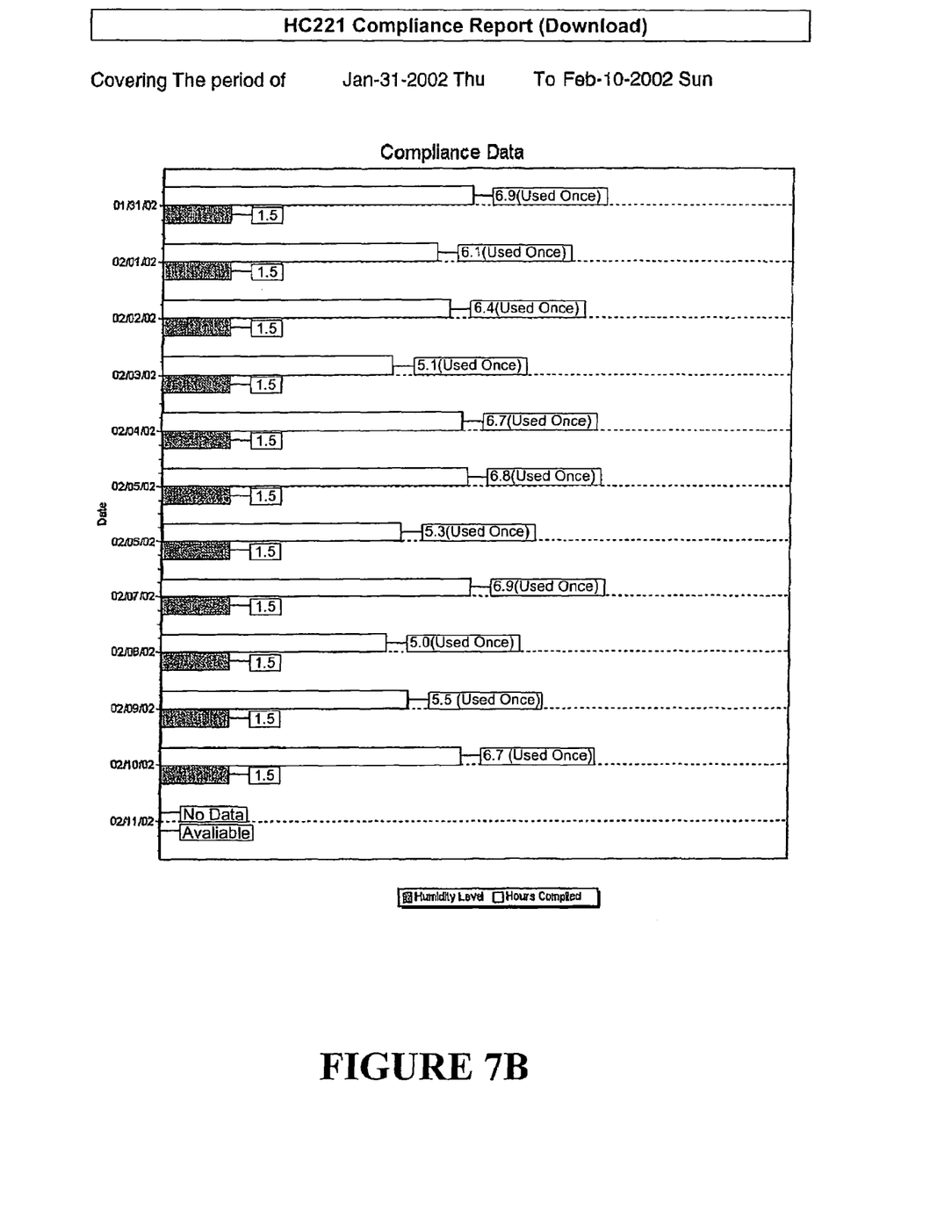
Figure 7C:
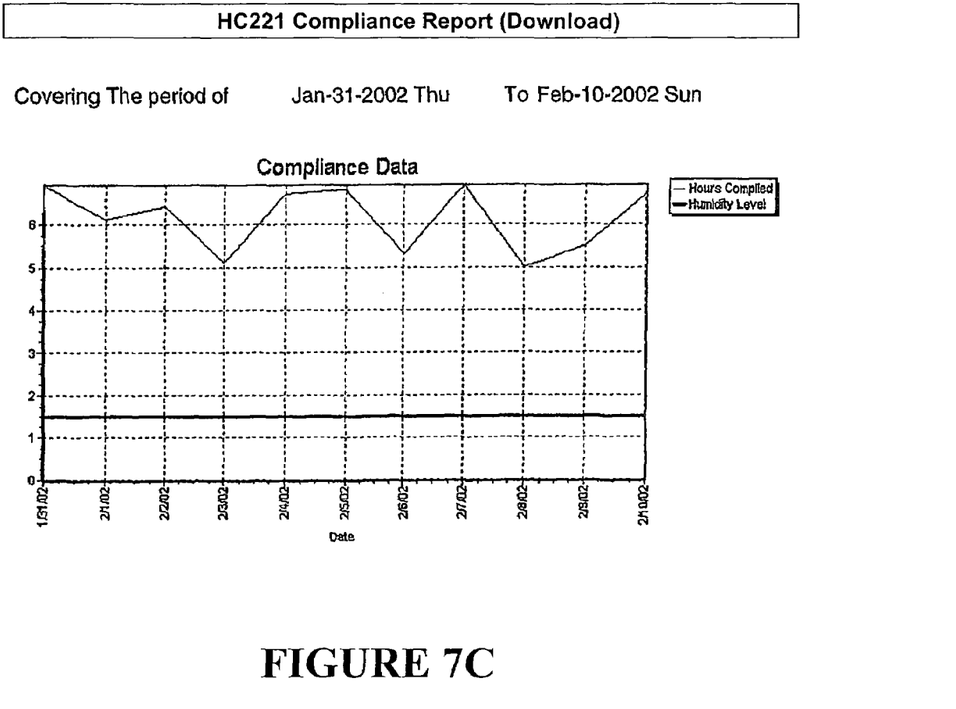

The reporting software further includes an interface for receiving the full data downloaded from the data store. Again the reporter software preferably records this data in a database together with pre-stored patient details and any historical data retrieved by either or both the LCD display reporting and data download. The reporter software is programmed to produce a report from the downloaded data, which report may be significantly more comprehensive than the report produced only from LCD display data. For example the report may include a bar graph of complied time and humidity setting for each day together with an indication of the number of times that a unit was turned on in that day. The reporter software may also produce equivalent line graphs, and/or scatter plots of hours complied plotted against humidity level for each therapy session. A sample report generated from full download data is shown in FIGS. 7A–7C.

Figure 6:
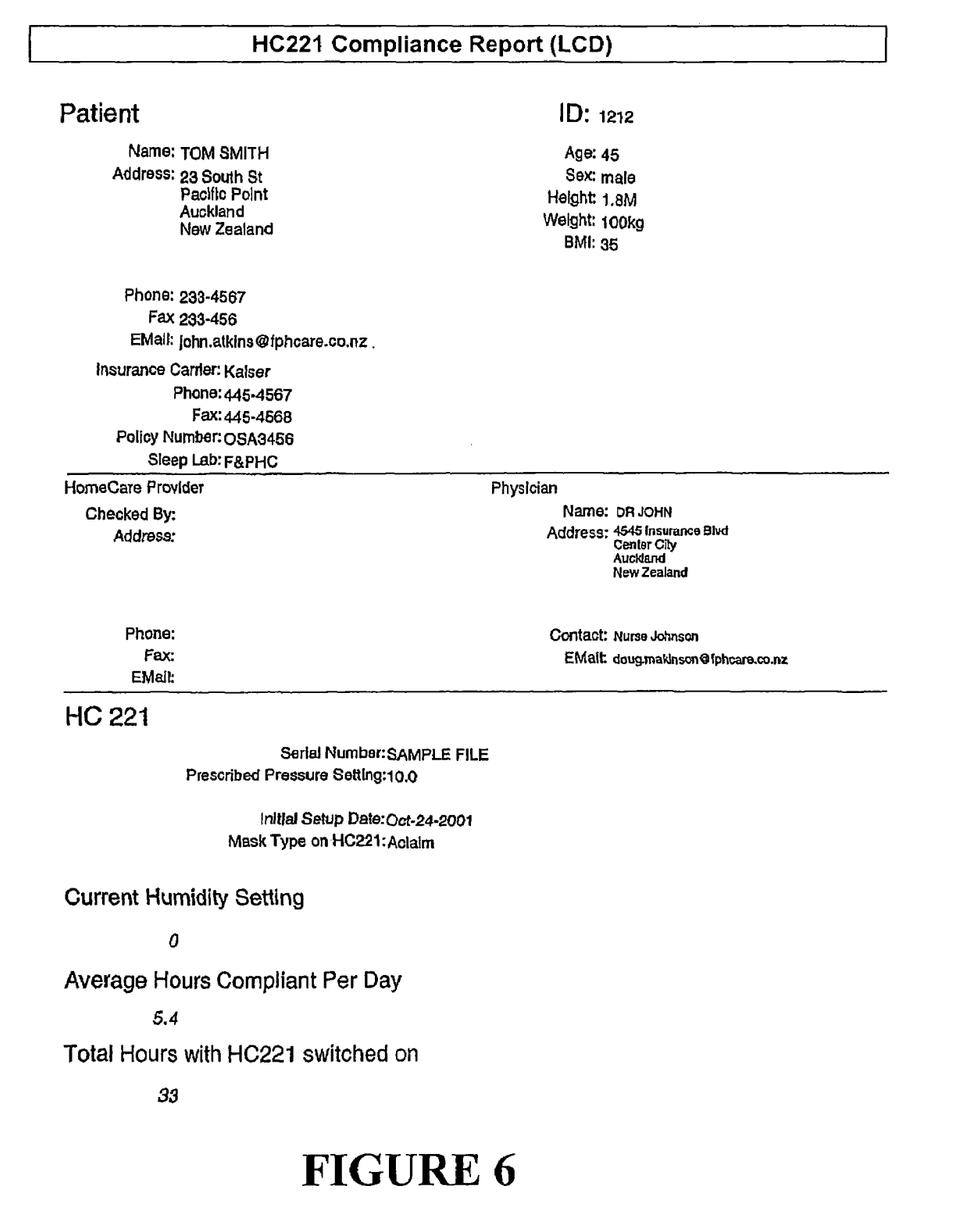
FIG. 6 is an example patient summary report based on compliance and humidity data as determined by surveying a user of a preferred apparatus according to the present invention.

From a report as in FIG. 6 a clinician will preferably look for an average complied hours per day of at least four hours as indicating effective therapy. Where the average complied hours is less than four hours or the patient is complaining of nasal symptoms, then, if warranted by the recorded humidity setting, the clinician may recommend increasing the humidity control setting. If the patient is complaining of excessive condensation and this corresponds with the recorded humidity control setting the clinician may suggest reducing the humidity control setting. Where adverse symptoms seem to contradict the recorded humidity control setting this may indicate an apparatus malfunction requiring service.

With a report based on full data download the clinician may readily identify trends and relationships between humidity setting and compliance, and recommend humidity settings which correspond with improved compliance.

Persons skilled in the art will appreciate that significant variations will be made on the preferred embodiment of the present invention without departing from the general principal. For example the form of the gases delivery and humidification apparatus may be subject to considerable variation. Known forms of gases delivery equipment include open or closed loop fan or blower based devices, pressure regulated pump devices and pressure regulated draw off from a high pressure supply, amongst others. Humidification may be by heated water bath, microporous humidifiers or moisture exchange device amongst others. In the preferred embodiment including a water bath humidifier, direct recordal of the humidifier setting is chosen for convenience. In other humidifier forms alternative estimation of the delivered humidity may be used. For example drip or flow rate to a continuously replenished microporous humidifier, or device presence for a moisture exchange device. Alternatively delivered humidity may be directly sensed using a flow probe in the humidified gases delivery stream.

It will also be appreciated that numerous alternatives to or variations on the method of determining compliance are also available. Compliance may for example be determined by the alternative methods of leak detection, breathing cycle detection or pressure comparison (rather than flow comparison). Furthermore, it may be desirable to provide sufficient data storage capacity, or a continuous communication link between the apparatus and a remote data store, for the device to record or supply a more detailed compliance and humidity history. This could include a continuous or periodic record of compliance, or compliance changes, throughout a therapy session, and/or continuous or periodic humidity data, and/or data recording changes in indicated humidity, throughout the therapy sessions. For such purposes it may be advantageous to provide the apparatus with modem or LAN connections or with an internal modem for connection with a public telephone network, or a wireless telecommunications interface for local or remote network connection.

It is believed that recordal of data indicative of humidity, alone or together with data indicative of compliance by a user, provides valuable data for clinician analysis which can be used to improve compliance times by individual therapy users.

The invention claimed is:

1. Apparatus for delivery of humidified gases therapy, said apparatus including:
    a humidifier, said humidifier having a humidity setting selector, operable by said patent to set and adjust a desired humidity level;
    a blower, said blower having a range of operating speeds, and delivering a substantially constant pressure across a wide flow range, for an unvaried operating speed,
    a flow sensor providing an output indicative of flow delivered by said apparatus,
    means for producing user compliance data, calculated from said output of said flow sensor and said operating speed of said blower,
    data recording means, said data recording means recording humidity data and said user compliance data, said humidity data indicative of the humidity of gases delivered by the apparatus, and
    an output interface means for outputting said recorded user compliance data and humidity data.

2. An apparatus for delivery of humidified gases therapy as claimed in claim 1 wherein said humidity data is derived from said humidity setting.

3. An apparatus for delivery of humidified gases as claimed in claim 2 wherein said user compliance data is determined by comparing said output from said flow sensor to an upper flow limit and a lower flow limit appropriate for the operating speed at that time and recording the total time during the operating cycle of said apparatus when said output is within said upper flow limit and said lower flow limit.

4. An apparatus for delivery of humidified gases as claimed in claim 3 wherein said output indicative of flow delivered is recorded as an average flow over a set time period.

5. An apparatus for delivery of humidified gases as claimed in claim 4 wherein a compliance counter in said data recording means is incremented if said average flow is between said upper and lower limits over said time period.

6. An apparatus for delivery of humidified gases therapy as claimed in claim 1 wherein said humidity data is derived from a humidity sensor.

7. An apparatus for delivery of humidified gases as claimed in claim 6 wherein said user compliance data is determined by comparing said output from said flow sensor to an upper flow limit and a lower flow limit appropriate for the operating speed at that time, and recording the total time during the operating cycle of said apparatus when said output is within said upper flow limit and said lower flow limit.

8. An apparatus for delivery of humidified gases as claimed in claim 7 wherein said output indicative of flow delivered is recorded as an average flow over a set time period.

9. An apparatus for delivery of humidified gases as claimed in claim 8 wherein a compliance counter in said data recording means is incremented if said average flow is between said upper and lower limits over said time period.

10. An apparatus for delivery of humidified gases as claimed in claim 1 wherein said user compliance data is determined by comparing said output from said flow sensor to an upper flow limit and a lower flow limit appropriate for the operating speed at that time, and recording the total time during the operating cycle of said apparatus when said output is within said upper flow limit and said lower flow limit.

11. An apparatus for delivery of humidified gases as claimed in claim 10 wherein said output indicative of flow delivered is recorded as an average flow over a set time period.

12. An apparatus for delivery of humidified gases as claimed in claim 11 wherein a compliance counter in said data recording means is incremented if said average flow is between said upper and lower limits over said time period.

* * * * *

UNITED STATES PATENT AND TRADEMARK OFFICE
CERTIFICATE OF CORRECTION

PATENT NO. : 7,086,399 B2
APPLICATION NO. : 10/446594
DATED : August 8, 2006
INVENTOR(S) : Ian Douglas Makison, Alex Young and David Alan Bond It is certified that error appears in the above-identified patent and that said Letters Patent is hereby corrected as shown below:

Column 7, Line 53 "patent" should be -- patient --
Column 7, Line 54 "level;" should be -- level, --

Signed and Sealed this

Fifth Day of December, 2006

JON W. DUDAS
*Director of the United States Patent and Trademark Office*